United States Patent [19]

Scott

[11] Patent Number: 5,005,587
[45] Date of Patent: Apr. 9, 1991

[54] BRAID ELECTRODE LEADS AND CATHETERS AND METHODS FOR USING THE SAME

[75] Inventor: Steven E. Scott, Miami, Fla.

[73] Assignee: Telectronics Pacing Systems, Inc., Englewood, Co.

[21] Appl. No.: 434,246

[22] Filed: Nov. 13, 1989

[51] Int. Cl.$^5$ ............................................... A61N 1/05
[52] U.S. Cl. .................................. 128/786; 128/419 P
[58] Field of Search ..................... 128/642, 419 P, 784, 128/785, 786, 783

[56] References Cited

U.S. PATENT DOCUMENTS

| | | | |
|---|---|---|---|
| 4,033,357 | 7/1977 | Helland et al. | 128/785 |
| 4,176,660 | 12/1979 | Mylrea | 128/715 |
| 4,402,328 | 9/1983 | Doring | 128/785 |
| 4,444,206 | 4/1984 | Gold | 128/784 |
| 4,641,656 | 2/1987 | Smits | 128/419 P |
| 4,662,377 | 5/1987 | Heilman et al. | 128/419 P |

FOREIGN PATENT DOCUMENTS 8502779  7/1985  PCT Int'l Appl. .................. 128/786

OTHER PUBLICATIONS

I. W. P. Obel et al., "Electrode System for Closed Chest Ventricular Defibrillation", World Symposium, Jerusalem (1987).

"Temporary Pervenous Leads", Cordis Pacing System Catalog (1983).

"Cordis Ducor® Angiographic Catheters", Cordis Ducor® Catheters and the Angiographic System, Catalog (1982–1983).

Primary Examiner—William E. Kamm
Assistant Examiner—Scott M. Getzow
Attorney, Agent, or Firm—Gottlieb, Rackman & Reisman

[57] ABSTRACT

A lead or catheter for implantation in a body for conducting electrical current between an electrical device and a location in the body, including an elongate tubular insulating material, a first portion of electrically conductive braid forming a closely fitting sheath around a portion of the insulating material, an electrical coupling means for coupling the device to the lead and an electrically insulated connection means for electrically connecting the braid and the coupling means. A part of the electrically conductive braid is exposed for providing the electrical energy to the body. Preferably the electrically insulated connection means includes an integral portion of the braid surrounded by a tubular insulating member. The lead may be configured as an endocardial catheter, or may be used elsewhere in the body and have one or more fingers, each with a respective exposed portion of braid.

27 Claims, 3 Drawing Sheets

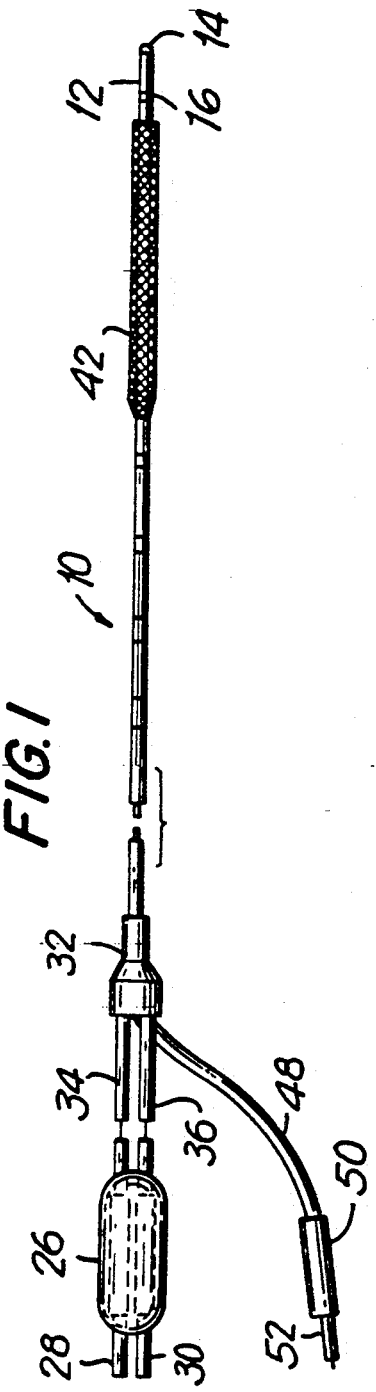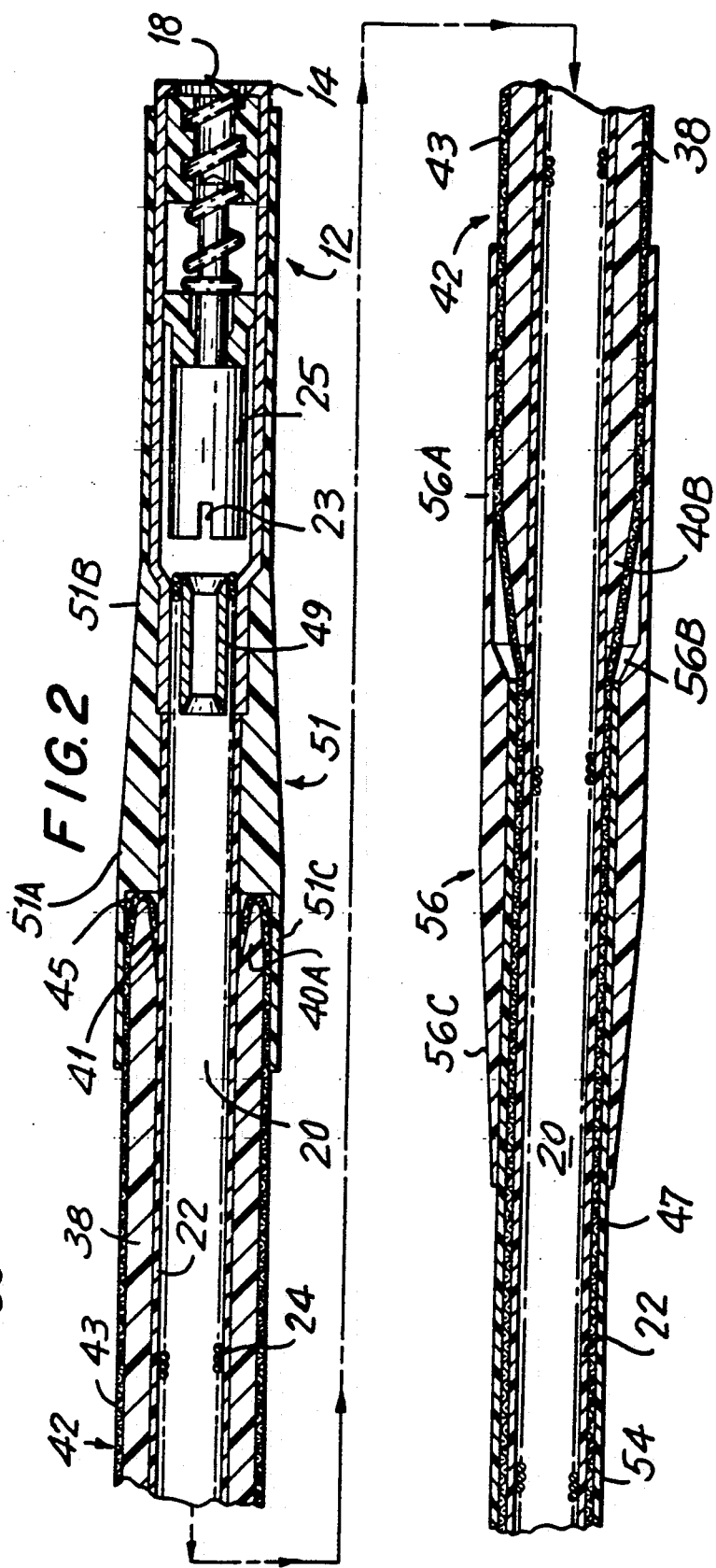

BRAID ELECTRODE LEADS AND CATHETERS AND METHODS FOR USING THE SAME

FIELD OF THE INVENTION

This invention is directed to an electrode system for use with an implantable defibrillator. In particular, it is directed to an electrode system which does not require entry into the chest cavity for implantation.

BACKGROUND ART

To date, most implanted defibrillation electrode systems used in patients have consisted of two flexible metal braid electrodes with an insulated backing. These so called patches are placed at implant on the epicardial or pericardial surface and generally held in placed with sutures. A less frequently used alternative system of electrodes uses one patch electrode placed epicardially or pericardially, and a wound metallic ribbon electrode carried on a catheter placed in the superior vena cava (SVA). The wound electrode is commonly known as a "spring electrode".

Both the "patch-patch" electrode system and the "spring-patch" electrode system suffer from the drawback of requiring major surgery under general anesthesia to implant. Electrode systems which do not require major surgery to implant are presently being explored by a number of researchers.

One such system consists of a multi-electrode catheter and an optional external patch electrode which is placed in a subcutaneous space. The catheter carries three electrodes: (1) a distal small area button tip electrode, (2) a large area spring electrode located just proximal of the distal button, and (3) a large area spring electrode located at some distance proximal to the tip. The spacing between electrode (2) and electrode (3) is such that when electrodes (1) and (2) are in the right ventricle, and electrode (1) is at the right ventricular apex, then electrode (3) will be in the high right atrium and/or the SVC.

The electrical connections of the catheter for an automatic implantable cardioverter defibrillator (AICD) generally utilize electrodes (1) and (2) for pacing, fibrillation sensing and rate sensing, and electrodes (2) and (3) for cardioverting, and defibrillation.

The catheter of this system is known to have the following disadvantages:

1. The catheter is "stiff" at the electrodes. This lack of flexibility is primarily due to the properties of the metallic ribbon.
2. The catheter does not always retain its position in the heart once implanted, as there is no action fixation mechanism at the distal end. While passive fixation may be used, this does not insure acute stability, which is important if the lead is also used for pacing.
3. Since the spacing of the electrodes is fixed, the location of electrode (3) in of the heart varies from patient to patient due to variations in the size of the heart. This may lessen defibrillation efficacy in some patients.
4. Insulator break may occur when there are two separate and distinct shocking electrodes in the same lead body and high energy shocks of opposite polarity are carried.
5. Clotting around the large diameter electrode has been reported.

DISCLOSURE OF THE INVENTION

It is a principal object of the invention to provide a catheter having a large surface area for the delivery of a countershock (i.e., a cardioverting or defibrillating shock to the heart.

It is another object of the invention to provide a catheter primarily for subcutaneous use which provides current at precisely controlled locations.

It is another principal object of the invention to provide an endocardial catheter including a defibrillation electrode with a large surface area.

It is another object of the invention to provide an endocardial defibrillation catheter which is flexible and of relatively small diameter.

In accordance with the invention a lead for implantation in the body for conducting a countershock from a source of electrical energy comprises an elongate cylindrical insulating material, a first portion of electrically conductive braid forming a closely fitting sheath around a portion of the insulating material, an electrical coupling means for coupling the source to the lead, and an electrically insulated connection means for electrically connecting the mesh and the electrical coupling means.

Also in accordance with the invention, an endocardial catheter is constructed so as to be capable of providing a countershock to a patient's heart. The catheter comprises an elongated insulating member; a first terminal means at one end of the member and a cylindrical braid electrode surrounding the member along a portion of the catheter. The electrode is disposed externally on the elongated member. A first electrical connection means connects the braid electrode to the first terminal means.

The braid electrode comprises a plurality of wire conductors. The conductors are helically wound about the elongate insulating member.

Also in accordance with the invention, the catheter further comprises a tip electrode at an end of the insulating member most distal from the first terminal means. A second terminal means and a second electrical connection means for connecting the tip electrode means to the second terminal means are provided.

In another embodiment of the invention a ring electrode surrounds the insulating member proximate the tip electrode. A third terminal means and third electrical connection means for connecting the ring electrode to the third terminal means are also provided.

Two versions of these catheters may be produced. One version is suitable for use in the right ventricle. Another version is suitable for use in the right atrium.

Also in accordance with the invention, the endocardial catheter is used in combination with either a large surface area patch counter-electrode, or an elongate tubular counter-electrode, adapted for subcutaneous implantation in proximity to the heart. The fourth electrode connection means has a first end connected to the selected subcutaneous electrode, and a second end. A fourth terminal means is connected to the second end of the fourth electrical connection means.

The elongate counter-electrode insulating member comprises an elongate insulating inner tube; an elongate insulated outer tube surrounding the inner tube; and the first electrical connection means is preferably a cylindrical braid disposed between the inner tube and the outer tube.

Another embodiment of the invention is a lead comprising a plurality of electrically insulating elongate members; for each of said members, a respective tubular braid electrode surrounding one of said elongate members; a mechanical connection means for mechanically connecting said plurality of members; and an electrical connection means for electrically connecting said braid electrodes to one another and to said electrical coupling means. This lead may be used a subcutaneously.

The invention is also directed to a method for providing electrical stimulation to a patient's heart comprising implanting an endocardial catheter including an exposed braid electrode along a portion of its length; providing an additional electrode positioned so that current can flow through the patient between said braid electrode and said additional electrode; and electrically connecting said braid electrode and said additional electrode to a source of electrical stimulation energy.

BRIEF DESCRIPTION OF THE DRAWINGS

Further objects, features and advantages of the invention will become apparent upon consideration of the following detailed description in conjunction with the drawings, in which:

FIG. 1 is a plan view of a temporary tripolar catheter for use in the right ventricle in accordance with the invention;

FIG. 2 is an enlarged cross-sectional view of the distal end of a permanent embodiment of a bipolar catheter in accordance with the invention;

DETAILED DESCRIPTION OF THE DRAWINGS

Figures 3, 4, 6:
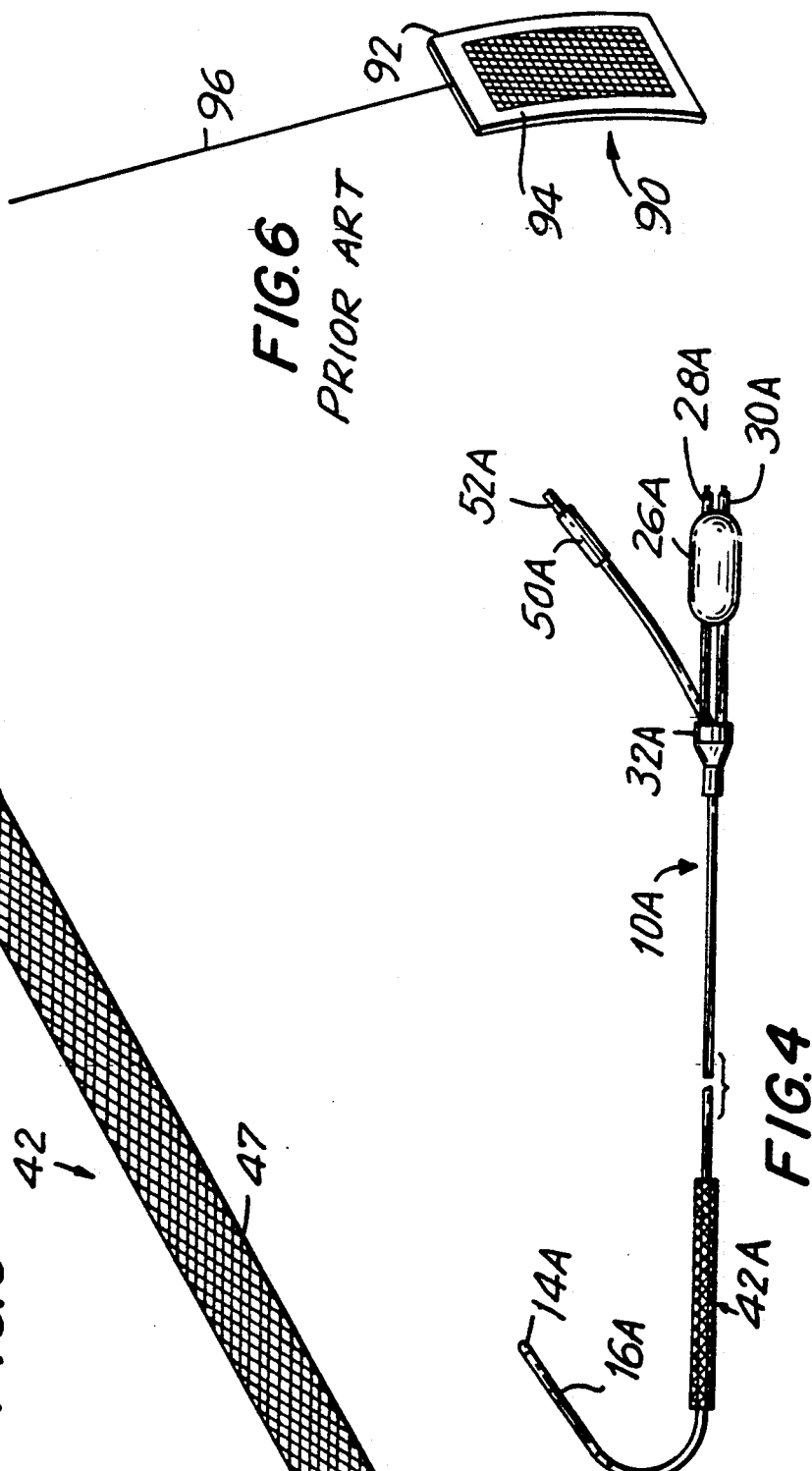
FIG. 3 is a perspective view of the braid used in the catheter of FIG. 2.
FIG. 4 is a plan view of a temporary atrial "J" embodiment of the invention.
FIG. 6 is a perspective view of a prior art subcutaneous patch electrode which may be used with the invention.

Although the present invention is described and illustrated primarily with respect to a ventricular endocardial catheter, it will be understood by those skilled in the art that the principles of the invention can be applied to an atrial catheter as well.

Referring to FIG. 1, a temporary tripolar endocardial defibrillation and pacing catheter 10 includes a conventional tip assembly 12 having a distal tip electrode 14 and a band or ring electrode 16 for pacing and sensing, as is well known in the art. As is also well known, tip electrode 14 and ring electrode 16 may be formed of a platinum-iridium alloy covered with porous platinum.

The construction of catheter 10, as a temporary catheter, may be based on a Ducor polyurethane tube having two small lumens and one large lumen.

Electrical connection is made to tip electrode 14 and ring electrode 16 by two separate wire conductors. Each conductor extends along the length of one of the lumens of catheter 10 and terminates in a connector 26 of a type well known in the art. Connector 26 includes pins 28 and 30 which are received in the neck of an appropriate electronic module such as a brady-cardia support pacemaker or other device for providing electrical stimulation of the heart or for recording signals therefrom. Catheter 10 includes a hub or Y connector 32 from which separate polyurethane tubes 34 and 36 extend to connector 26. The wire conductors extend through hub 32 and then through respective tubes 34 and 36, thus providing electrical connection to one of pins 28 and 30.

In accordance with the invention, catheter 10 has placed, externally along a portion of its length, a cylindrical braid electrode 42. Electrical connection to electrode 42 is made by collapsing the portion of the braid not used as electrode 42 into a rope, and passing the rope through a small opening into the large lumen. This rope conductor extends into an insulating tube 48 having a first end terminating in hub 32 and a second end terminating in a defibrillator connector 50. Connector 50 has a connection pin 52 extending therefrom. Connection pin 52 is electrically connected to the end of the rope conductor.

Referring to FIG. 2, a permanent bipolar catheter 11 is illustrated. An active fixation device such as a helical spring 18 is normally received within tip assembly 12. Helical spring 18 may be extended to protrude from tip assembly 12 when an appropriate activating member or stylet (not shown) disposed in lumen 20 of an inner insulating tube 22 engages a slot 23 in a rotationally supported driving member 25, and is rotated, as is well known in the art. A wire coil conductor 24 extends longitudinally within tube 22 to electrically connect electrode 14 with a suitable connector (not shown) similar to connector 26 of FIG. 1. A nine centimeter length of Silastic ® tube 38 is placed over inner tube 22. The inner diameter of tube 38 is sized so as to have a tight fit when adhered over inner tube 22, while the outer diameter is selected to be approximately that of tip assembly 12. Tube 38 has a double conical taper at distal end 40A; that is, the outer diameter tapers inwardly and the inner diameter tapers outwardly. There is a circumferential space 41 of substantially triangular cross section between the most distal portion of tube 38 and inner tube 22. Tube 38 has a simple conical taper of its outer diameter at proximal end 40B. Inner tube 22 and Silastic ® tube 38 are surrounded by a cylindrical braid 42 (FIG. 3). Braid 42 has a distal portion 43 with a diameter which fits snugly over tube 38. The most distal portion 45 of braid 42 is folded into space 41 between the outer surface of inner tube 22 and the tapered inner surface of tube 38. After this is done, tip assembly 12 is crimped to the distal end of inner tube 22 at crimp region 49.

A Silastic ® sleeve 51 is then placed over a portion of crimp region 49 and the distal end of tube 38 to insulate the proximal shank of the pacing electrode 14 and to isolate the ends of the braided wires from the patient's body. Sleeve 51 has a main cylindrical portion 51A with an internal diameter that fits tightly around inner tube 22. Cylindrical portion 51A tapers at its distal end to a second cylindrical portion 51B which fits tightly around a proximal portion of crimp region 49. A third proximal cylindrical portion 51C of sleeve 51 fits tightly around the distal portion of braid 42. Prior to placement of sleeve 51, Dow Corning medical adhesive is applied to the portion of braid 42 which is surrounded by cylindrical portion 51C of sleeve 51.

A reduced diameter proximal portion 47 of braid 42 surrounds inner tube 22. The diameter of the proximal portion 47 of braid 42 is selected so that it fits snugly about inner tube 22.

A catheter in accordance with the invention may be terminated in various ways, as is well known in the art. If braid 42 is to be terminated in a bifurcated manner, as illustrated with respect to FIG. 1, inner tube 22 may be removed from the braid approximately nine centimeters from its proximal end. The remaining portion of braid 42 is then inserted into insulating tube 48 and electrically connected to connection pin 52.

If a linear termination (not shown) for braid 42, rather than a bifurcated termination, is desired, it is necessary that the proximal portion of braid 42 surrounds tubes 22 along virtually its entire length. A terminal pin is used for the conductor associated with the tip electrode. A terminal ring may be used to terminate the braid.

A polyurethane outer tube 54 is placed over braid 42 and positioned so that its distal end is adjacent to the proximal end of the Silastic ® tube 38, with braid 42 passing between the adjacent ends of outer tube 54 and tube 38. A molded sleeve 56 formed of polyurethane is placed over the transition region. Sleeve 56 has a first substantially cylindrical portion 56A which internally tapers at 56B to a proximal portion 56C having a cylindrical inner surface. The outer surface of proximal portion 56C tapers in the proximal direction until its diameter is substantially that of outer tube 54. Sleeve 56 is secured with Dow Corning medical adhesive which is applied to its inner surface prior to placement on catheter 10.

Thus, between sleeve 51 and sleeve 56 the wire braid electrode is exposed over a longitudinal distance of approximately 6 cm and available to deliver a cardioverting or defibrillation shock. The favorable results achieved with this design are discussed in greater detail below.

In the design illustrated in FIG. 2 the braid is used as both a conductor and an electrode. While a separate conducting wire may be welded to the braid, using the braid as both conductor and electrode simplifies fabrication and favorably resolves difficulties which might otherwise arise due to corrosion.

Referring to FIG. 3, braid 42 is comprised of sixteen titanium wires having a diameter of 0.003 inches (0.076 mm) wound at forty eight picks per inch to define a helix angle of approximately 40 degrees. Eight of the wires are wound in a first direction and the other eight are wound in a second direction. Preferably an electroplated platinum coating is formed over the titanium surface of the wires. Alternatively, the wires may be formed of a platinum-iridium alloy. Braid 42 is tapered at 53 so that it follows the outer contour of sleeve 38 and is annealed prior to assembly to reduce stress and provide the greatest possible longevity.

Referring to FIG. 4, an atrial temporary braid endocardial catheter 10A has a spherical pacing tip electrode 14A formed of 316 stainless steel. The ring electrode 16A is formed of a 90% platinum 10% iridium alloy. The braid 42A is formed of titanium and, as is the case for the embodiments illustrated in FIG. 1 and FIG. 2, continues from the 6 centimeter long braid electrode to serve as the conductor. The pacing and sensing terminal pins 28A and 30A, which extend from a connector 26A similar to connector 26, are formed of brass and gold plated. The tubes of the catheter body are formed from Ducor polyurethane.

The pacing and sensing electrodes 14A and 16A are of the same type as those used for a standard temporary pacing catheter. The pin 52A which is connected to the defibrillator output, similar to pin 52, is formed of titanium.

Figure 5:
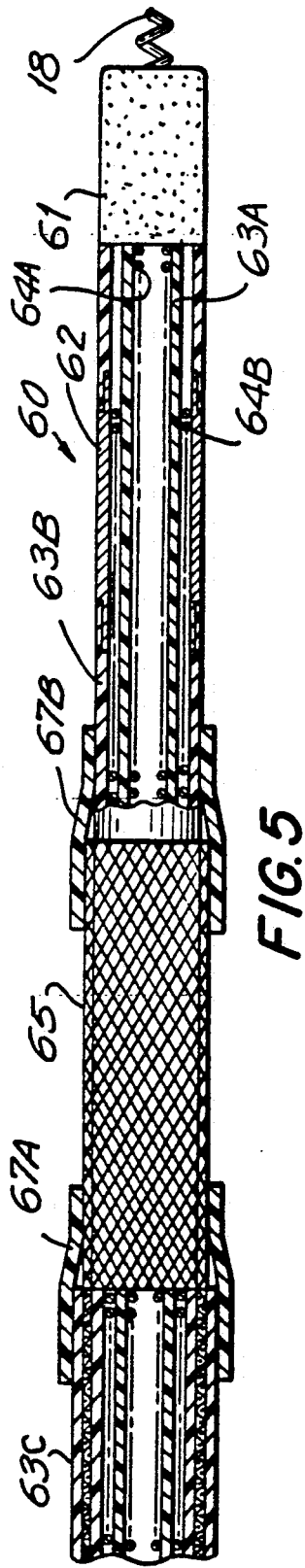
FIG. 5 is an enlarged cross-sectional view of the distal end of a permanent tripolar catheter in accordance with the invention.

FIG. 5 illustrates a preferred construction for a permanent tripolar braid electrode defibrillation catheter 60. The construction is similar to that of a bipolar pacing catheter having an active fixation member 18, a porous tip electrode 61 and an anode band 62. Disposed in the lumen of a first polyurethane tube 63A is a conductor 64A which extends to tip electrode 61. A second conductor 64B surrounds tube 63A and extends to anode band 62. Conductor 64B is surrounded by a second insulating tube 63B which extends to anode band 62. A cylindrical braid electrode 65 extends along a portion of the length of catheter 60 but is surrounded, at all except for its most distal 6 centimeters, by a polyurethane tube 63C which serves to insulate the unexposed portions of braid electrode 65 from the body. Tightly fitting and adhered elastic tubing sleeves 67A and 67B provide smooth transitions between components of different diameters.

Electrical connections at the proximal end of catheter 60 may be made in a manner similar to that illustrated for temporary tripolar catheter 10 of FIG. 1.

All of the endocardial catheters using a braid electrode are advantageous in that they provide a very large surface area for the application of an electrical shock but do not abraid the cardiac tissue. Fibrotic tissue growth on and between the wires of the braid occurs. While such tissue growth tends to minimize any abrasiveness that might otherwise result from the geometry of the braid, it has been found that it does not interfere with the efficient delivery of a defribillation shock, i.e., it does not raise the defibrillation threshold.

Referring to FIG. 6, a subcutaneous patch electrode 90 having an insulated back 92 and an active face wire mesh electrode 94 is illustrated. An insulated electrical conductor 96 extends from patch electrode 90 and terminates at a defibrillation connector (not shown) similar to connector 50 and having a titanium pin similar to pin 52 extending therefrom.

A defibrillation system in accordance with the invention may use one or more catheters having a braid electrode. When two catheters are used, one is a ventricular catheter and the other an atrial catheter. These catheters may be used alone or in conjunction with one or two subcutaneous electrodes.

Figure 7:
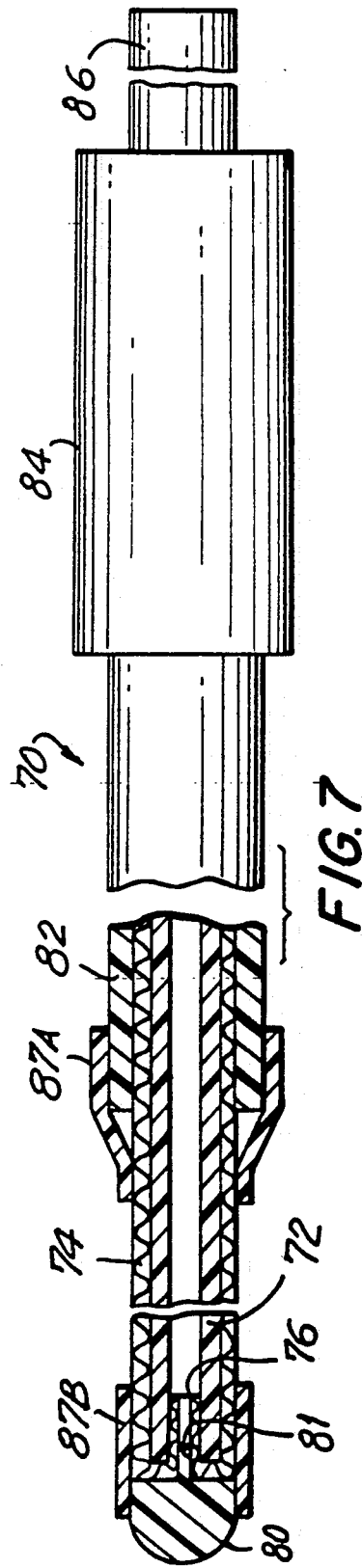
FIG. 7 is an enlarged view, in partial cross-section, of a first embodiment of a subcutaneous lead in accordance with the invention.

FIG. 7 illustrates an embodiment of the invention which is most useful as a subcutaneous electrode to be used in conjunction with an endocardial lead having a braid electrode according to the invention. A lead 70 includes an inner tube 72 surrounded by a braid 74. A small length 76 of the most distal portion of braid 74 surrounds the distal end of tube 72. Length 76 is forced into lumen 78 of tube 72. Lead 70 is terminated at its most distal end by a Silastic ® cap 80, having a domed or spherical shape. Silastic ® cap 80, having a cylindrical portion 81 which extends into inner tube 72, is secured in place with a suitable medical adhesive of the type described above. An outer tube 82 of an insulating material such as Silastic ® or polyurethane covers most of the length of lead 70, leaving only a length of approximate 9 cm of braid 74 exposed. Tightly fitting and adhered elastic tubing sleeves 87A and 87B provide smooth transitions between components of different diameters. The lead is terminated by a conventional connector 84 having an electrically conducting pin 86, as is well known in the art.

Lead 70 of FIG. 7 is especially advantageous for use subcutaneously at a portion of the thorax adjacent the heart. It is particularly advantageous in that only a small surgical incision in the skin is necessary for placement of the lead. Preferably the exposed portion of braid 74 is located in one of the intercostal spaces and is therefore less likely to produce complications in those patients of low weight. However, where appropriate, the exposed portion of braid 74 may be placed over a rib. Defibrillation threshold energy does not appear to vary significantly between placement in an intercostal space and placement over a rib. The braid is secured in place by suturing to the musculature. If deemed advantageous, a plurality of these single electrode leads may be utilized in a particular patient.

Figure 8:
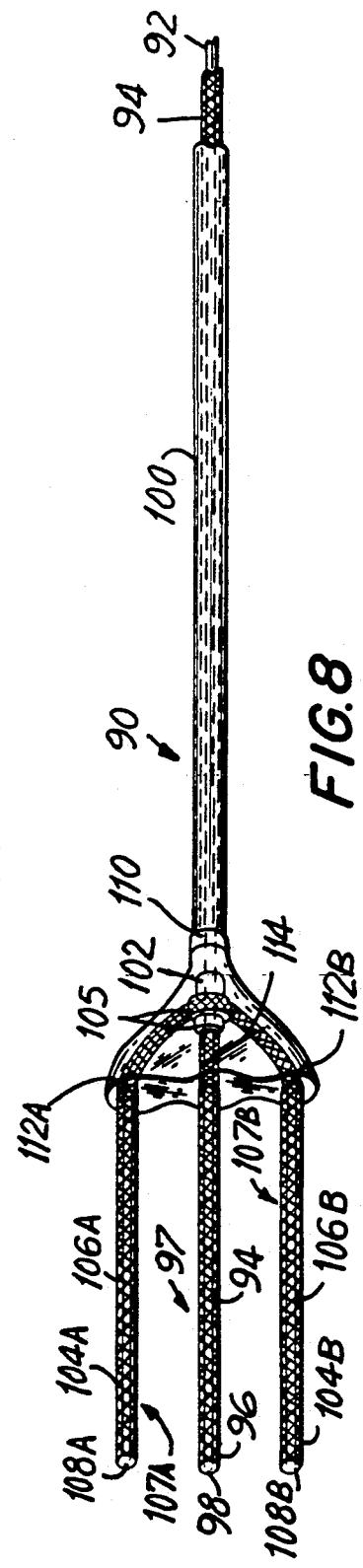
FIG. 8 is a plan view, in partial cross-section, of a second embodiment of a subcutaneous lead in accordance with the invention.

Referring to FIG. 8, another embodiment, a lead 90 in accordance with the invention, which can be utilized subcutaneously, is illustrated. An inner tube 92 formed of a Silastic ® or polyurethane material is surrounded by a braid 94 and extends to a distal end 96 to form a finger 97. Inner tube 92 and braid 94 are terminated by a Silastic ® cap 98 in a manner identical to the termination of lead 70 of FIG. 7. An outer insulating tube 100 formed of polyurethane or Silastic ® fits snugly about the proximal portion of braid 94.

The proximal ends of each of two braids 104A and 104B are wrapped around the external surface of a metallic connecting sleeve 102, which is fitted snugly about braid 94. Braids 104A and 104B are cut to dimensions slightly longer than the distance from distal end 96 to connecting sleeve 102. Brazing is used so as to mechanically and electrically connect braid 94, sleeve 102, braid 104A and braid 104B.

Respective tubes 106A and 106B, preferably formed of the same material as inner tube 92, and having a length somewhat shorter than the distance from distal end 96 to connecting sleeve 102, are fitted within braids 104A and 104B, respectively to form fingers 107A and 107B of stiffness comparable to that of finger 97.

The distal ends of fingers 107A and 107B are terminated by caps 108A and 108B, respectively, in the same manner as lead 70 of FIG.7. A portion of the lead 90 including the distal end 110 of outer tube 100, extends distally to a region 105. Collapsed portions of braids 104A and 104B extend past the proximal ends of tubes 106A and 106B and therefore the proximal ends 112A and 112B of fingers 107A and 107B. These components are then all held in a mold (not shown) having a cavity into which a Silastic material is placed so as to form a trifurcation member 114.

It is intended that fingers 97, 107A and 107B have lateral spacing between them so that they may be fitted into adjacent intercostal spaces. Thus, a small taper angle may be established between outer tube 100 and fingers 107A and 107B.

In a preferred method of use, a first tripolar catheter, e.g., the catheter 60 of FIG. 5, is placed with a tip in the right ventricular apex (RVA). The braid electrode 42 and tip and ring electrodes 14 and 16 are thus disposed in the right ventricular chamber. The tip and ring electrodes are used for sensing the right ventricular electrogram and, if necessary, for antitachycardia or bradycardia pacing. The braid electrode is used for cardioverting or defibrillating in conjunction with other electrodes as described below.

Preferably a second catheter is placed in the right atrium so that its braid electrode is located in the high right atrium or in the superior vena cava (SVC). The second catheter may be of a construction identical to the first. Alternatively, the second catheter may be designed with a spacing between the ring and sleeve electrode which is different than in the first catheter. In addition the second catheter may be designed with a preformed "J" shape similar to that commonly used in certain atrial pacing catheters.

In the atrium the tip and ring electrodes may be used for pacing and sensing in a variety of modes. These include dual chamber bradycardia pacing, atrial antitachycardia pacing and discrimination of ventricular tachycardia from supraventricular tachycardia or exercise tachycardia. The braid electrode of the second catheter may be used for cardioverting and defibrillating.

According to the preferred method one or more subcutaneous electrodes is also used. These electrodes are placed outside the chest cavity but in proximity to the heart. The two catheter braid electrodes and one or two subcutaneous electrodes are connected in a selected combination for the application of cardioverting or defibrillating countershock. Various combinations of electrodes and countershocks have been described in the literature. These include single current pathways, simultaneous dual current pathways, sequential shocks and biphasic shocks.

A second method of using the present invention utilizes one catheter according to the invention placed in the right ventricle and one or more subcutaneous electrodes. The electrode countershock is applied between the catheter braided sleeve electrode and the subcutaneous electrodes. Ventricular pacing and sensing is accomplished by using the bipolar tip and ring electrodes. Atrial sensing and pacing may be accomplished if a second, optional catheter of the type ordinarily used in bradycardia pacing is placed in the atrium.

A third method utilizes one endocardial catheter according to the invention placed in the right atrium and one or more subcutaneous electrodes. A second catheter of the type ordinarily used in bradycardia pacing is placed in the right ventricle for sensing and pacing. Cardioverting or defibrillating countershocks are applied between the braided sleeve of the catheter and the subcutaneous electrodes.

The current technique for implanting a non-thoracotomy defibrillation catheter system involves the following: First, the transvenous defibrillation catheter is implanted in the right ventricle (RV). Then, the thorax is "mapped" with an R2 electrode to optimize the position for the subcutaneous patch. Mapping requires that several defibrillation thresholds (DFTs) be found for various R2 placements using a temporary endocardial defibrillation catheter. The location of the R2 which offers the lowest DFT is where the subcutaneous patch electrode is placed. The catheters are then tunneled through the thorax and connected to the generator. The entire procedure is very time consuming and tedious to the patient.

The above procedure may be further optimized if mapping and system implant take place on different days. This is most easily accomplished by using a temporary version of the catheter according to the invention, e.g., the catheter 10 of FIG. 1, in conjunction with an R2 electrode for mapping.

In addition to defibrillation catheter system implants, a temporary catheter in accordance with the invention may also serve as a research tool for evaluating patients and catheter configurations as well as a routine electrophysiologic catheter to be used as a safeguard during procedures involving patients prone to ventricular or atrial fibrillation (VF or AF).

For hospitalized or bedridden patients requiring defibrillation, an endocardial lead in accordance with the invention may be used with one or more cutaneous defibrillation electrodes. The energy required for defibrillation is reduced.

Thus, it can be seen that the invention described above provides a number of improvements over the existing endocardial catheter and catheter and patch defibrillation electrode systems. In particular the braid electrode contributes very little stiffness to the catheter. The section of the catheter containing the braid electrode is nearly as flexible as the portion away from the braid and may be constructed so as to be of small diameter. For example, temporary versions of a lead according to the invention may have a size of 7 Fr or even smaller. The unit Fr indicates French gauge and corresponds to three times the diameter of the lead in millimeters. Permanent versions may have a size of 8 Fr. Further, permanent versions of the catheter accept a stylet which can be used to temporarily stiffen and shape the catheter to facilitate implantation. In addition, the presence of the multiconductor braid provides a large surface area with a multitude of high field intensity points which facilitates effective defibrillation and provides a reasonably low defibrillation threshold. A braid electrode may also be used for pacing, with a relatively small area flexible braid electrode replacing a relatively large area, stiff band electrode. Finally, the multiconductor braid is inherently "failure tolerant" in that there are multiple electrical conduction paths. Thus a break in one or even several of the braid wires would not result in a failure of the lead.

Although the invention has been described with reference to specific embodiments, it is to be understood that these embodiments are merely illustrative of the application of the principles of the invention. Numerous modifications may be made therein and other arrangements may be devised without departing from the spirit and scope of the invention.

What is claimed is:

1. A lead for implantation in a body for conducting an electrical current between an electrical device and a location in the body, said lead comprising:
   an elongate tubular insulating member;
   a first exposed portion of electrically conductive braid forming a closely fitting sheath around a portion of said insulating material;
   a first electrical coupling means for coupling said device to said lead; and
   a first electrically insulated connection means for electrically connecting said braid and said electrical coupling means,
   said tubular insulating member having a part which extends distally with respect to said electrical coupling means from said braid, further comprising:
   an electrode on said part, said electrode being spaced apart from said braid;
   a second electrical coupling means for electrically coupling said device to said lead; and
   a second electrical connection means for electrically connecting said electrode to said second electrical coupling means.

2. The lead of claim 1, wherein said electrode is an annular ring disposed along said part of said insulating member which extends distally.

3. The lead of claim 1, wherein said electrode is disposed at an end of said part of said insulating member which extends distally.

4. An endocardial catheter for providing a countershock to a patient's heart, said catheter comprising:
   an elongate member formed of an insulating material;
   a first terminal means at one end of said elongate member for connection to a source of electricity;
   a tubular braid electrode surrounding said elongate member along a portion of said catheter, said electrode being disposed externally on said elongate member;
   first electrical connection means for connecting said braid electrode to said terminal means;
   a tip electrode at an end of said insulating member most distal from said first terminal means;
   a second terminal means; and
   a second electrical connection means for connecting said tip electrode to said second terminal means.

5. The endocardial catheter of claim 4, further comprising;
   a ring electrode surrounding said insulating member proximate said tip electrode;
   a third terminal means; and
   a third electrical connection means for connecting said ring electrode to said third terminal means.

6. The endocardial catheter of claim 5, in combination with:
   a patch electrode adapted for subcutaneous implantation in proximity to the heart;
   fourth electrical connection means having a first end connected to said subcutaneous patch electrode and a second end; and
   a fourth terminal means connected to said second end of said fourth electrical connection means.

7. A combination for providing a countershock to a patient's heart, said combination comprising a catheter and a subcutaneous lead, said catheter comprising:
   an elongate member formed of an insulating material;
   a first terminal means at one end of said elongate member for connection to a source of electricity;
   a tubular braid electrode surrounding said elongate member along a portion of said catheter, said electrode being disposed externally on said elongate member; and
   a first electrical connection means for connecting said braid electrode to said terminal means, said lead comprising:
   an elongate tubular insulating material;
   a first portion of electrically conductive braid forming a closely fitting sheath around a portion of said insulating material;
   an electrical coupling means for coupling said source to said leads; and
   electrically insulated connection means for electrically connecting said braid and said electrical coupling means.

8. A combination for providing a countershock to a patient's heart, said combination comprising a catheter and a subcutaneous lead, said catheter comprising:
   an elongate member formed of an insulating material;

a first terminal means at one end of said elongate member for connection to a source of electricity;

a tubular braid electrode surrounding said elongate member along a portion of said catheter, said electrode being disposed externally on said elongate member; and first electrical connection means for connecting said braid electrode to said terminal means, said lead comprising:

a plurality of electrically insulating elongate members;

for each of said elongate members, a respective tubular braid electrode surrounding one of said elongate members;

a mechanical connection means for mechanically connecting said plurality of elongate members;

an electrical coupling means for coupling said lead to said source of electrical energy; and an electrical connection means for electrically connecting said braid electrodes to one another and to said electrical coupling means.

9. The combination of claim 8, wherein said elongate insulating member of said catheter comprises:

an elongate insulating inner tube; and an elongate insulating outer tube surrounding said inner tube.

10. The combination of claim 9, wherein said first electrical connection means is a cylindrical electrically conductive braid disposed between said inner tube and said outer tube.

11. The combination of claim 10, wherein said electrically conductive braid is an integral extension of said braid electrode.

12. The combination of claim 9, wherein said inner tube has a lumen extending along its length, further comprising an active fixation means for affixing a distal end of the lead to an interior surface of the heart, said lumen being for providing access to said active fixation means from a proximal end of said lead.

13. A lead for implantation in the body for conducting a countershock from a source of electrical energy, comprising:

a plurality of electrically insulating elongate members;

for each of said elongate members, a respective tubular braid electrode surrounding one of said elongate members;

a mechanical connection means for mechanically connecting said plurality of members, an electrical coupling means for coupling said lead to said source of electrical energy; and an electrical connection means for electrically connecting said braid electrodes to one another and to said electrical coupling means.

14. The lead of claim 13, wherein said electrical connection means includes a first portion for electrically connecting said respective braid electrodes to one another and a second portion extending from said braid electrodes to said electrical coupling means.

15. The lead of claim 14, further comprising an insulating tube extending from said electrical coupling means to said mechanical connection means to insulate said first portion from the body.

16. The lead of claim 13, wherein said mechanical connection means is formed of an insulating material and insulates portions of said tubular braid electrodes extending between said elongate members to thereby insulate said portions from the body.

17. The lead of claim 13, wherein said mechanical connection means is shaped to connect said insulating members so that said insulating members extend substantially parallel to one another from said mechanical connection means.

18. The lead of claim 17, wherein said mechanical connection means is configured so that said insulating members are spaced from one another to fit into successive intercostal spaces of a patient.

19. The lead of claim 13, wherein said mechanical connection means is shaped to connect said insulating members so that said insulating members diverge slightly from one another in a distal direction from said mechanical connection means.

20. The lead of claim 13, in combination with affixing means for subcutaneously affixing the insulating members covered with the respective braid electrodes.

21. The lead of claim 20, wherein said affixing means are sutures.

22. The lead of claim 13, in combination with affixing means for affixing the insulating members covered with respective braid electrodes to the heart.

23. The lead of claim 22, wherein said affixing means are sutures.

24. A method for providing electrical stimulation to a patient's heart comprising:

implanting an endocardial catheter having an exposed braid electrode along a portion of its length in the patient's heart;

providing a lead having an additional electrode along a portion of its length, said electrode being positioned so that current can flow through the patient between said braid electrode and said additional electrode; and electrically connecting said braid electrode and said additional electrode to a source of electrical stimulation energy.

25. The method of claim 24, further comprising placing said additional electrode cutaneously.

26. The method of claim 24, further comprising placing said additional electrode subcutaneously.

27. The method of claim 24, further comprising placing said additional electrode subcutaneously and wherein said additional electrode comprises a braid electrode.

* * * * *